United States Patent
Satchivi et al.

(10) Patent No.: US 9,101,136 B2
(45) Date of Patent: Aug. 11, 2015

(54) SYNERGISTIC HERBICIDE/FUNGICIDE COMPOSITION CONTAINING CERTAIN PYRIDINE CARBOXYLIC ACIDS AND CERTAIN FUNGICIDES

(75) Inventors: Norbert M. Satchivi, Westfield, IN (US); Paul R. Schmitzer, Indianapolis, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 275 days.

(21) Appl. No.: 13/029,253

(22) Filed: Feb. 17, 2011

(65) Prior Publication Data

US 2011/0207607 A1 Aug. 25, 2011

Related U.S. Application Data

(60) Provisional application No. 61/306,066, filed on Feb. 19, 2010.

(51) Int. Cl.
| | |
|---|---|
| A01N 43/40 | (2006.01) |
| A01N 25/32 | (2006.01) |
| A01N 35/04 | (2006.01) |
| A01N 37/34 | (2006.01) |
| A01N 37/50 | (2006.01) |
| A01N 43/30 | (2006.01) |
| A01N 43/42 | (2006.01) |
| A01N 43/46 | (2006.01) |
| A01N 43/54 | (2006.01) |
| A01N 43/653 | (2006.01) |
| A01N 47/14 | (2006.01) |
| A01N 47/18 | (2006.01) |
| A01N 47/24 | (2006.01) |
| A01N 47/34 | (2006.01) |
| A01N 47/38 | (2006.01) |

(52) U.S. Cl.
CPC .................................. *A01N 43/40* (2013.01)

(58) Field of Classification Search
CPC ...................................................... A01N 43/40
USPC ........................................................ 504/105
See application file for complete search history.

(56) References Cited

U.S. PATENT DOCUMENTS

| | | | |
|---|---|---|---|
| 5,087,764 A | | 2/1992 | Reiffenrath et al. |
| 7,314,849 B2 | | 1/2008 | Balko et al. |
| 7,622,641 B2 | | 11/2009 | McCutchen et al. |
| 2003/0060371 A1* | | 3/2003 | Asrar et al. ................ 504/272 |
| 2004/0192924 A1 | | 9/2004 | Meyer et al. |
| 2008/0242546 A1 | | 10/2008 | Schultz et al. |

FOREIGN PATENT DOCUMENTS

| | | |
|---|---|---|
| WO | 0016627 A1 | 3/2000 |
| WO | WO2007082098 A2 | 7/2007 |
| WO | 2009147205 A2 | 12/2009 |
| WO | PCT/US2011/025160 | 5/2011 |

OTHER PUBLICATIONS

Anonymous, Mixtures of Fungicides and Herbicides, Research Disclosure No. 348074, Apr. 1993, Research Disclosure, 5 pages.*
Stump, William, Azoxystrobin and Post Emergence Herbicide Combinations for Rhizoctonia and Weed Management in Sugarbeet, Jan.-Jun. 2002, Post Emergence Herbicide Combinations, pp. 37-58.*

* cited by examiner

*Primary Examiner* — John Pak
*Assistant Examiner* — Andriae M Holt
(74) *Attorney, Agent, or Firm* — Michael J. Terapane; Meunier Carlin & Curfman, LLC

(57) ABSTRACT

An herbicide/fungicide composition containing (a) a pyridine carboxylic acid component and (b) a fungicide component provides synergistic control of selected weeds.

37 Claims, No Drawings

SYNERGISTIC HERBICIDE/FUNGICIDE COMPOSITION CONTAINING CERTAIN PYRIDINE CARBOXYLIC ACIDS AND CERTAIN FUNGICIDES

CROSS REFERENCE TO RELATED APPLICATIONS

This application claims the benefit of U.S. Provisional Patent Application Ser. No. 61/306,066 filed Feb. 19, 2010, which is expressly incorporated by reference herein.

FIELD OF THE INVENTION

This invention concerns a synergistic herbicidal composition containing (a) an herbicidal pyridine carboxylic acid component and (b) at least one fungicide selected from the group consisting of azoxystrobin, carbendazim, chlorothalonil, cyproconazole, cyprodinil, epoxiconazole, fenpropidin, flutriafol, iprodione, kresoxim-methyl, mancozeb, metconazole, metrafenone, picoxystrobin, prochloraz, propiconazole, proquinazid, prothioconazole, pyraclostrobin, quinoxyfen, spiroxamine, tebuconazole, tetraconazole, thiophanate-methyl, trifloxystrobin, and a picolinamide.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Similarly, the protection of crops from fungi which destroy or disfigure crops is also a constantly recurring problem in agriculture. To help combat this problem, researchers in the field of synthetic chemistry have produced an extensive variety of chemicals and chemical formulations effective in the control of such fungi. Chemical herbicides and fungicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Eighth Edition, 2002, p. 462, "'synergism' [is] an interaction of two or more factors such that the effect when combined is greater than the predicted effect based on the response to each factor applied separately." The present invention is based on the discovery that certain fungicides and certain pyridine carboxylic acids, already known individually for their fungicidal and herbicidal efficacy, display a synergistic herbicidal effect when applied in combination.

SUMMARY OF THE INVENTION

The present invention concerns a synergistic herbicide/fungicide mixture comprising an herbicidally effective amount of (a) a pyridine carboxylic acid herbicide of the formula (I)

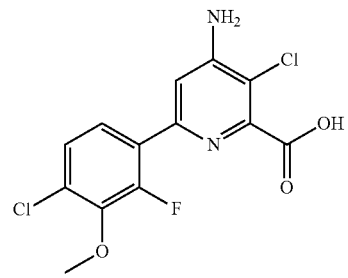

and agriculturally acceptable salts, esters and amides of the carboxylic acid, and (b) a fungicide selected from the group consisting of azoxystrobin, carbendazim, chlorothalonil, cyproconazole, cyprodinil, epoxiconazole, fenpropidin, flutriafol, iprodione, kresoxim-methyl, mancozeb, metconazole, metrafenone, picoxystrobin, prochloraz, propiconazole, proquinazid, prothioconazole, pyraclostrobin, quinoxyfen, spiroxamine, tebuconazole, tetraconazole, thiophanate-methyl, trifloxystrobin, and a picolinamide fungicide of formula (II).

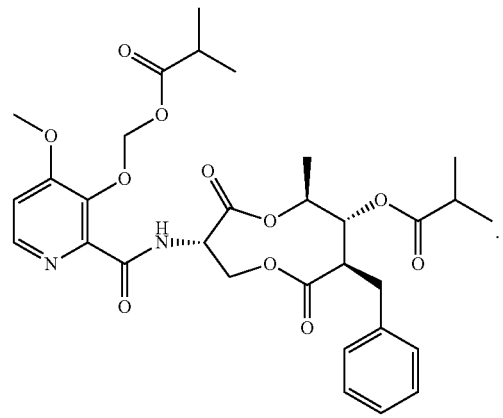

The compositions may also contain an agriculturally acceptable adjuvant or carrier. The synergistic compositions may also generally be employed in combination with known herbicide safeners, particularly with cloquintocet-mexyl.

The present invention also concerns herbicidal/fungicidal compositions for and methods of controlling the growth of undesirable vegetation, particularly in cereals and the use of these synergistic compositions.

4-Amino-3-chloro-6-(4-chloro-2-fluoro-3-methoxyphenyl)pyridine-2-carboxylic acid (I) is used for the control of weeds in cereal crops including spring, winter and durum wheat, and spring and winter barley.

It has been surprisingly found that a combination of a strobilurin fungicide, such as azoxystrobin, kresoxim-methyl, picoxystrobin, pyraclostrobin or trifloxystrobin, and the pyridine carboxylic acid of the formula (I) exhibits a synergistic action in the control of kochia (*Kochia scoparia* L; KCHSC), scented mayweed (*Matricaria chamomila* L; MATCH), wild pansy (*Viola tricolor* L; VIOTR), bird's-eye speedwell (*Veronica persica* L; VERPE), Russian thistle (*Salsola iberica* L; SASKR), redroot pigweed (*Amaranthus retroflexus* L; AMARE), lamb's-quarter (*Chenopodium album* L; CHEAL), chickweed (*Stellaria media* L; STEME) and Canada thistle (*Cirsium arvense* L; CIRAR) at application rates lower than the rates of the individual compounds.

It has also been surprisingly found that a mixture of a triazole fungicide, such as cyproconazole, epoxiconazole, flutriafol, metconazole, propiconazole, prothioconazole tebuconazole or tetraconazole, and the pyridine carboxylic acid of the formula (I) exhibits a synergistic action in controlling kochia (*Kochia scoparia* L; KCHSC), scented mayweed (*Matricaria chamomila* L; MATCH), wild pansy (*Viola tricolor* L; VIOTR), bird's-eye speedwell (*Veronica persica* L; VERPE), Russian thistle (*Salsola iberica* L; SASKR), redroot pigweed (*Amaranthus retroflexus* L; AMARE), lamb's-quarter (*Chenopodium album* L; CHEAL), chickweed (*Stellaria media* L; STEME) and Canada thistle (*Cirsium arvense* L; CIRAR) at application rates lower than the rates of the individual compounds.

The mixtures of an imidazole fungicide, such prochloraz, and the pyridine carboxylic acid of the formula (I) unexpectedly exhibit a synergistic action in control kochia (*Kochia scoparia* L; KCHSC), scented mayweed (*Matricaria chamomila* L; MATCH), wild pansy (*Viola tricolor* L; VIOTR), bird's-eye speedwell (*Veronica persica* L; VERPE) and Russian thistle (*Salsola iberica* L; SASKR) at application rates lower than the rates of the individual compounds.

It has also been surprisingly found that a mixture of a dithiocarbamate fungicide such as mancozeb, and the pyridine carboxylic acid of the formula (I) exhibits a synergistic action in control of kochia (*Kochia scoparia* L; KCHSC), scented mayweed (*Matricaria chamomila* L; MATCH), bird's-eye speedwell (*Veronica persica* L; VERPE), wild pansy (*Viola tricolor* L; VIOTR) and Russian thistle (*Salsola iberica* L; SASKR) at application rates lower than the rates of the individual compounds.

It has also been found that the mixture of an aromatic fungicide such as chlorothalonil, and the pyridine carboxylic acid of the formula (I) shows a synergistic action in control of kochia (*Kochia scoparia* L; KCHSC), scented mayweed (*Matricaria chamomila* L; MATCH), wild pansy (*Viola tricolor* L; VIOTR), bird's-eye speedwell (*Veronica persica* L; VERPE) and Russian thistle (*Salsola iberica* L; SASKR) at application rates lower than the rates of the individual compounds.

The mixture of a quinoline fungicide, such as quinoxyfen, and the pyridine carboxylic acid of the formula (I), exhibits a synergistic control of kochia (*Kochia scoparia* L; KCHSC), scented mayweed (*Matricaria chamomila* L; MATCH), wild pansy (*Viola tricolor* L; VIOTR), bird's-eye speedwell (*Veronica persica* L; VERPE) and Russian thistle (*Salsola iberica* L; SASKR) at application rates lower than the rates of the individual compounds.

It has also been found that the mixture of a fungicide such as spiroxamine, and the pyridine carboxylic acid of the formula (I) shows a synergistic action in control of wild pansy (*Viola tricolor* L; VIOTR) at application rates lower than the rates of the individual compounds.

It has also been unexpectedly found that the mixture of a benzimidazole fungicide, such as carbendazim, and the pyridine carboxylic acid of the formula (I) shows a synergistic action in control of wild pansy (*Viola tricolor* L; VIOTR) at application rates lower than the rates of the individual compounds.

It has also been surprisingly found that the mixture of a quinazolinone fungicide such as proquinazid, and the pyridine carboxylic acid of the formula (I) shows a synergistic action in control of wild pansy (*Viola tricolor* L; VIOTR) at application rates lower than the rates of the individual compounds.

The mixture of the picolinamide fungicide of formula (II) and the pyridine carboxylic acid of the formula (I), exhibits a synergistic control of kochia (*Kochia scoparia* L; KCHSC), scented mayweed (*Matricaria chamomila* L; MATCH) and wild pansy (*Viola tricolor* L; VIOTR) at application rates lower than the rates of the individual compounds.

It has also been unexpectedly found that the combination of an anilinopyrimidine fungicide such as cyprodinil, and the pyridine carboxylic acid of the formula (I) shows a synergistic action in control of Russian thistle (*Salsola iberica* L; SASKR) at application rates lower than the rates of the individual compounds.

It has also been found that the mixture of a benzophenone fungicide such as metrafenone, and the pyridine carboxylic acid of the formula (I) shows a synergistic action in control of scented mayweed (*Matricaria chamomila* L; MATCH), wild pansy (*Viola tricolor* L; VIOTR) and Russian thistle (*Salsola iberica* L; SASKR) at application rates lower than the rates of the individual compounds.

It has also been surprisingly found that a mixture of a piperidine fungicide, such as fenpropidin, and the pyridine carboxylic acid of the formula (I) exhibits a synergistic action in controlling wild pansy (*Viola tricolor* L; VIOTR), redroot pigweed (*Amaranthus retroflexus* L; AMARE), lamb's-quarter (*Chenopodium album* L; CHEAL) and Canada thistle (*Cirsium arvense* L; CIRAR) at application rates lower than the rates of the individual compounds.

It has also been surprisingly found that a mixture of a dicarboximide fungicide, such as iprodione, and the pyridine carboxylic acid of the formula (I) exhibits a synergistic action in controlling wild pansy (*Viola tricolor* L; VIOTR), redroot pigweed (*Amaranthus retroflexus* L; AMARE) and Canada thistle (*Cirsium arvense* L; CIRAR) at application rates lower than the rates of the individual compounds.

It has also been surprisingly found that a mixture of a thiophanate fungicide, such as thiophanate-methyl, and the pyridine carboxylic acid of the formula (I) exhibits a synergistic action in controlling wild pansy (*Viola tricolor* L; VIOTR), redroot pigweed (*Amaranthus retroflexus* L; AMARE), lamb's-quarter (*Chenopodium album* L; CHEAL), chickweed (*Stellaria media* L; STEME) and Canada thistle (*Cirsium arvense* L; CIRAR) at application rates lower than the rates of the individual compounds.

DETAILED DESCRIPTION OF THE INVENTION

A number of pyridine carboxylic acid compounds are described in U.S. Pat. No. 7,314,849 B2, including 4-amino-3-chloro-6-(4-chloro-2-fluoro-3-methoxyphenyl)pyridine-2-carboxylic acid methyl. The pyridine carboxylic acid of the formula (I) controls annual grass weeds including *Setaria, Pennisetum,* and *Echinochloa*; broadleaf weeds such as *Papaver, Galium, Lamium, Kochia, Amaranthus, Aeschynomene, Sesbania,* and *Monochoria*; and sedge species such as *Cyperus* and *Scirpus*.

Azoxystrobin is the common name for methyl ($\alpha$E)-2-[[6-(2-cyanophenoxy)-4-pyrimidinyl]oxy]-$\alpha$-(methoxymethylene)benzeneacetate. Its fungicidal activity is described in *The Pesticide Manual*, Fourteenth Edition, 2006. Azoxystrobin controls a wide range of pathogens including *Septoria tritici, Leptoshaeria nodorum* and *Pyrenophora teres* in cereal crops.

Carbendazim is the common name for methyl 1H-benzimidazol-2-ylcarbamate. Its fungicidal activity is described in *The Pesticide Manual*, Fourteenth Edition, 2006. Carbendazim controls *Septoria, Fusarium, Erysiphe* and *Pseudocercosporella* in cereal crops.

Chlorothalonil is the common name for 2,4,5,6-tetrachloro-1,3-benzenedicarbonitrile. Its fungicidal activity is described in *The Pesticide Manual*, Fourteenth Edition, 2006. Chlorothalonil controls a wide range of fungal diseases in a wide range of crops including cereals.

Cyproconazole is the common name for α-(4-chlorophenyl)-α-(1-cyclopropylethyl)-1H-1,2,4-triazole-1-ethanol. Its fungicidal activity is described in *The Pesticide Manual*, Fourteenth Edition, 2006. Cyproconazole controls *Septoria*, rust, powdery mildew, *Rhynchosporium, Cercospora* and *Ramularia* in cereals and sugar beet.

Cyprodinil is the common name for 4-cyclopropyl-6-methyl-N-phenyl-2-pyrimidinamine Its fungicidal activity is described in *The Pesticide Manual*, Fourteenth Edition, 2006. Cyprodinil controls *Erysiphe, Pyrenophora, Rhynchosporium, Tapesia, Botritys a* in cereals and grapes, field crops and ornamentals.

Epoxiconazole is the common name for rel-1-[[(2R,3S)-3-(2-chlorophenyl)-2-(4-fluorophenyl)oxiranyl]methyl]-1H-1,2,4-triazole. Its fungicidal activity is described in *The Pesticide Manual*, Fourteenth Edition, 2006. Epoxiconazole controls diseases caused by Ascomycetes, Basidomycetes and Deuteromycetes in cereals and sugar beet.

Fenpropidin is the common name for (±)-1-[3-[4-(1,1-dimethylethyl)phenyl]-2-methylpropyl]piperidine. Its fungicidal activity is described in *The Pesticide Manual*, Fourteenth Edition, 2006. Fenpropidin controls a wide range of diseases including powdery mildew (*Erysiphe graminis*), rusts (*Puccinia* spp.), leaf spots (*Rhynchosporium secalis*) in cereals.

Flutriafol is the common name for α-(2-fluorophenyl)-α-(4-fluorophenyl)-1H-1,2,4-triazole-1-ethanol. Its fungicidal activity is described in *The Pesticide Manual*, Fourteenth Edition, 2006. Flutriafol controls a wide spectrum of leaf and ear diseases, including *Erysiphe graminis, Septoria* spp., *Puccinia* spp., *Helminthosporium teres, Helmintosporium tritici-repentis* and *Rhynschosporium secalis* in cereals.

Iprodione is the common name for 3-(3,5-dichlorophenyl)-N-(1-methylethyl)-2,4-dioxo-1-imidazolidine=carboxamide. Its fungicidal activity is described in *The Pesticide Manual*, Fourteenth Edition, 2006. Iprodione controls *Botrytis, Fusarium, Rhizoctonia* in cereals.

Kresoxim-methyl is the common name for methyl (αE)-α-(methoxyimino)-2-[(2-methylphenoxy)methyl]benzeneacetate. Its fungicidal activity is described in *The Pesticide Manual*, Fourteenth Edition, 2006. Kresoxim-methyl controls mildew, scald, net blotch and glume blotch on cereals.

Mancozeb is the common name for [[2-[(dithiocarboxy)amino]ethyl]carbamo-dithioato(2⁻)-κS,κS']manganese mixture with [[2-[(dithiocarboxy)amino]ethyl]carbamo-dithioato(2⁻)-κS,κS']zinc. Its fungicidal activity is described in *The Pesticide Manual*, Fourteenth Edition, 2006. Mancozeb controls many fungal diseases in a wide range of crops including in cereals.

Metconazole is the common name for 5-[(4-chlorophenyl)methyl]-2,2-dimethyl-1-(1H-1,2,4-triazol-1-ylmethyl)cyclopentanol. Its fungicidal activity is described in *The Pesticide Manual*, Fourteenth Edition, 2006. Metconazole controls wide range of foliar diseases on cereal crops.

Metrafenone is the common name for (3-bromo-6-methoxy-2-methylphenyl)(2,3,4-trimethoxy-6-methylphenyl)methanone. Its fungicidal activity is described in *The Pesticide Manual*, Fourteenth Edition, 2006. Metrafenone controls *Pseudocercosporella, Erisyphe* in cereals.

Picoxystrobin is the common name for methyl (E)-(α)-(methoxymethylene)-2-[[[6-(trifluoromethyl)-2-pyridinyl]oxy]methyl]benzeneacetate. Its fungicidal activity is described in *The Pesticide Manual*, Fourteenth Edition, 2006. Picoxystrobin controls a broad-spectrum of diseases including *Mycosphaerella graminicola, Puccinia recondita, Helminthosporium tritici-repentis, Erysiphe graminis* in cereals.

Prochloraz is the common name for N-propyl-N-[2-(2,4,6-trichlorophenoxy)ethyl]-1H-imidazole-1-carboxamide. Its fungicidal activity is described in *The Pesticide Manual*, Fourteenth Edition, 2006. Prochloraz controls a wide range of diseases affecting field crops, fruit, turf and vegetables.

Propiconazole is the common name for 1-[[2-(2,4-dichlorophenyl)-4-propyl-1,3-dioxolan-2-yl]methyl]-1H-1,2,4-triazole. Its fungicidal activity is described in *The Pesticide Manual*, Fourteenth Edition, 2006. Propiconazole controls diseases caused by *Cochliobolus sativus, Erysiphe graminis, Leptosphaeria nodorum, Puccinia* spp., *Septoria* spp., *Pyrenophora teres, Pyrenophora tritici-repentis* and *Rhynchosporium secalis* in cereals.

Proquinazid is the common name for 6-iodo-2-propoxy-3-propyl-4(3H)-quinazolinone. Its fungicidal activity is described in *The Pesticide Manual*, Fourteenth Edition, 2006. Proquinazid controls powdery mildew in cereals.

Prothioconazole is the common name for 2-[2-(1-chlorocyclopropyl)-3-(2-chlorophenyl)-2-hydroxypropyl]-1,2-dihydro-3H-1,2,4-triazole-3-thione. Its fungicidal activity is described in *The Pesticide Manual*, Fourteenth Edition, 2006. Prothioconazole controls eyespot, *Fusarium* ear blight, leaf blotch diseases, rust and powdery mildew in wheat, barley and other crops.

Pyraclostrobin is the common name for methyl[2-[[[1-(4-chlorophenyl)-1H-pyrazol-3-yl]oxy]methyl]phenyl]methoxycarbamate. Its fungicidal activity is described in *The Pesticide Manual*, Fourteenth Edition, 2006. Pyraclostrobin controls major plant pathogens, such as *Septoria tritici, Puccinia* spp., *Drechslera tritici-repentis* and *Pyrenophora teres* in cereals.

Quinoxyfen is the common name for 5,7-dichloro-4-(4-fluorophenoxy)quinoline. Its fungicidal activity is described in *The Pesticide Manual*, Fourteenth Edition, 2006. Quinoxyfen controls powdery mildew in cereals.

Spiroxamine is the common name for 8-(1,1-dimethylethyl)-N-ethyl-N-propyl-1,4-dioxaspiro[4.5]decane-2-methanamine. Its fungicidal activity is described in *The Pesticide Manual*, Fourteenth Edition, 2006. Spiroxamine controls powdery mildew in cereals.

Tebuconazole is the common name for α-[2-(4-chlorophenyl)ethyl]-α-(1,1-dimethylethyl)-1H-1,2,4-triazole-1-ethanol. Its fungicidal activity is described in *The Pesticide Manual*, Fourteenth Edition, 2006. Tebuconazole controls numerous pathogens in various crops, including *Puccinia* spp., *Erysiphe graminis, Septoria* spp., *Pyrenophora* spp., *Cochliobolus sativus, Fusarium* spp. and *Rhynchosporium secalis* in cereals.

Tetraconazole is the common name for (±)-1-[2-(2,4-dichlorophenyl)-3-(1,1,2,2-tetrafluoroethoxy)propyl]-1H-1,2,4-triazole. Its fungicidal activity is described in *The Pesticide Manual*, Fourteenth Edition, 2006. Tetraconazole controls powdery mildew, rusts, bunt and loose smut in cereals.

Thiophanate-methyl is the common name for dimethyl[1,2-phenylenebis(iminocarbonothioyl)]bis[carbamate]. Its fungicidal activity is described in *The Pesticide Manual*, Fourteenth Edition, 2006. Thiophanate-methyl controls a wide range of diseases including eyespot, powdery mildew in cereals.

Trifloxystrobin is the common name for methyl (αE)-α-(methoxyimino)-2-[[[[(1E)-1-[3-(trifluoromethyl)phenyl]

ethylidene]amino]oxy]methyl]benzeneacetate. Its fungicidal activity is described in *The Pesticide Manual*, Fourteenth Edition, 2006. Trifloxystrobin is used in cereals to control Ascomycetes, Basidomycetes, Deuteromycetes and Oomycetes.

The picolinamide fungicide of formula (II), or compound II, is isobutyric acid (3S,6S,7R,8R)-8-benzyl-3-[(3-isobutyryloxymethoxy-4-methoxypyridine-2-carbonyl)-amino]-6-methyl-4,9-dioxo-[1,5]dioxonan-7-yl ester. The compound of formula (II)

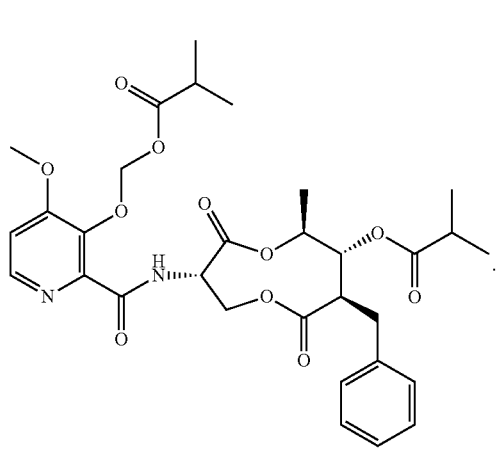

(II)

is described in U.S. Pat. No. 6,861,390.

The term herbicide is used herein to mean an active ingredient that kills, controls or otherwise adversely modifies the growth of plants. An herbicidally effective or vegetation-controlling amount is an amount of active ingredient which causes an adversely modifying effect and includes deviations from natural development, killing, regulation, desiccation, retardation, and the like. The terms plants and vegetation include germinant seeds, emerging seedlings, plants emerging from vegetative propagules, and established vegetation.

The term fungicide is used herein to mean an active ingredient that kills, controls or otherwise adversely affects the growth of fungi. A fungicidally effective amount is an amount of active ingredient which causes an adverse effect to a fungus and includes deviations from natural development, killing, regulation, and the like.

Herbicidal activity is exhibited by the compounds of the synergistic mixture when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

In the composition of this invention, the weight ratio of the pyridine carboxylic acid of formula (I) component to the fungicide component at which the herbicidal effect is synergistic lies within the range of between about 3.5:1 and about 1:1200.

The rate at which the synergistic composition is applied will depend upon the particular type of weed to be controlled, the degree of control required, and the timing and method of application. In general, the composition of the invention can be applied at an application rate of between about 10 grams per hectare (g/ha) and about 1235 g/ha based on the total amount of active ingredients in the composition. Depending upon the particular fungicide used, the fungicide component is applied at a rate between about 60 g/ha and about 1200 g/ha and the pyridine carboxylic acid of formula (I) component is applied at a rate between about 1 g/ha and about 35 g/ha, and the safener component, when used, is applied at a rate between about 0.05 g/ha and about 35 g/ha.

The components of the synergistic mixture of the present invention can be applied either separately or as part of a multipart herbicidal system.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition of the present invention include: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, orthodichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, xylachlor.

The synergistic composition of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the synergistic composition of the present invention in combination with herbicides that are selective for the crop being treated and which complement the spectrum of weeds controlled by these compounds at the application rate employed. It is further generally preferred to apply the synergistic composition of the present invention and other complementary herbicides at the same time, either as a combination formulation or as a tank mix.

The synergistic composition of the present invention can generally be employed in combination with known herbicide safeners, such as benoxacor, benthiocarb, brassinolide, cloquintocet (mexyl), cyometrinil, cyprosulfamate, daimuron, dichlormid, dicyclonon, dietholate, dimepiperate, disulfoton, fenchlorazole-ethyl, fenclorim, flurazole, fluxofenim, furilazole, isoxadifen-ethyl, mefenpyr-diethyl, mephenate, MG 191, MON 4660, naphthalic anhydride (NA), oxabetrinil, R29148 and N-phenyl-sulfonylbenzoic acid amides, to enhance their selectivity. Cloquintocet (mexyl) is a particularly preferred safener for the synergistic compositions of the present invention, specifically antagonizing any harmful effect of the synergistic compositions on rice and cereals.

In practice, it is preferable to use the synergistic composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rape seed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include: toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the synergistic composition of the present invention is generally from 0.001 to 98 percent by weight. Concentrations from 0.01 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.0001 to 1 weight percent active ingredient and preferably contain 0.001 to 0.05 weight percent.

The present compositions can be applied to weeds or their locus by the use of conventional ground or aerial dusters, sprayers, and granule applicators, by addition to irrigation or paddy water, and by other conventional means known to those skilled in the art.

The following examples illustrate the present invention.

EXAMPLES

Evaluation of Postemergence Herbicidal Activity of Mixtures in Cereal Crops

Seeds of the desired test plant species were planted in Sun Gro MetroMix 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of a cereal fungicide compound (as listed in Tables 1 through 34) and the cereal herbicide, 4-amino-3-chloro-6-(4-chloro-2-fluoro-3-methoxyphenyl) pyridine-2-carboxylic acid, alone and in combination. Weighed amounts of acid, esters (methyl) or salts (triethylammonium, TEA) of 4-amino-3-chloro-6-(4-chloro-2-fluoro-3-methoxyphenyl)pyridine-2-carboxylic acid (Compound I) were placed in 25 milliliter (mL) glass vials and dissolved in a volume of 97:3 volume-to-volume (v/v) acetone/dimethyl sulfoxide (DMSO) to obtain 4.5 milligrams active ingredient per milliliter (mg ai/mL) concentrated solutions. If Compound I did not dissolve readily, the mixture was warmed and/or sonicated. The concentrated solutions of Compound I were diluted to 1.5 mg ai/mL with the addition of 2 volumes of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio. A dilution solution was prepared by mixing 1 volume of 97:3 v/v acetone/DMSO and 2 volumes of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio. Compound requirements are based upon a 12 mL application volume at a rate of 187 liters per hectare (L/ha). The concentrated solutions of the cereal fungicides were prepared following the same procedure. Weighed amounts of fungicide were placed in 25 mL glass vials and dissolved in a volume of 97:3 v/v acetone/DMSO to obtain concentrated fungicide solutions. The concentrated solutions of the safener were prepared following the same procedure. Weighed amounts of safener were placed in 25 mL glass vials and dissolved in a volume of 97:3 v/v acetone/DMSO to obtain concentrated safener solutions.

Spray solutions of the cereal herbicide and the fungicidal compound mixtures were prepared by adding the concentrated solutions to the appropriate amount of dilution solution to form 12 mL spray solution with active ingredients in combinations. Spray solutions of the cereal herbicide, herbicide safener and the fungicidal compound mixtures were prepared by adding the concentrated solutions to the appropriate amount of dilution solution to form 12 mL spray solution with active ingredients in combinations.

Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 cm) above average plant canopy. Control plants were sprayed in the same manner with the solvent blank.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. Calculation of the synergistic and antagonistic response of herbicide combinations. *Weeds* 1967, 15, 20-22).

The following equation was used to calculate the expected activity of mixtures containing two active ingredients, A and B:

$$\text{Expected} = A + B - (A \times B / 100)$$

A = observed efficacy of active ingredient A at the same concentration as used in the mixture B = observed efficacy of active ingredient B at the same concentration as used in the mixture Some of the compounds tested, application rates employed, plant species tested, and results are given in Tables 1 through 39.

TABLE 1

Synergistic Activity of Compound I and Azoxystrobin on Several Key Broadleaf Weeds in Cereal Crops

| Application Rate (g/ha) | | KCHSC | | VERPE | | VIOTR | |
|---|---|---|---|---|---|---|---|
| Compound I Methyl Ester | Azoxystrobin | Ob | Ex | Ob | Ex | Ob | Ex |
| 8.75 | 0 | 65 | — | 62 | — | 53 | — |
| 17.5 | 0 | 71 | — | 67 | — | 58 | — |
| 35 | 0 | 96 | — | 78 | — | 60 | — |
| 0 | 62.5 | | — | | — | | — |
| 0 | 250 | | — | | — | | — |
| 8.75 | 62.5 | 72 | 65 | 62 | 62 | 62 | 53 |
| 17.5 | 62.5 | 81 | 71 | 75 | 67 | 63 | 58 |
| 35 | 62.5 | 98 | 96 | 88 | 78 | 62 | 60 |
| 35 | 250 | 100 | 96 | 65 | 78 | 60 | 60 |

TABLE 2

Synergistic Activity of Compound I and Azoxystrobin on Several Key Broadleaf Weeds in Cereal Crops

| Application Rate (g/ha) | | KCHSC | | MATCH | | SASKR | | VIOTR | |
|---|---|---|---|---|---|---|---|---|---|
| Compound I TEA Salt | Azoxystrobin | Ob | Ex | Ob | Ex | Ob | Ex | Ob | Ex |
| 8.75 | 0 | 40 | | 40 | | 80 | | 23 | |
| 17.5 | 0 | 55 | | 67 | | 84 | | 40 | |
| 35 | 0 | 65 | | 73 | | 86 | | 47 | |
| 0 | 62.5 | 0 | | 0 | | 0 | | 0 | |
| 8.75 | 62.5 | 40 | 40 | 37 | 40 | 84 | 80 | 10 | 23 |
| 17.5 | 62.5 | 60 | 55 | 80 | 67 | 89 | 84 | 50 | 40 |
| 35 | 62.5 | 87 | 65 | 84 | 73 | 89 | 86 | 62 | 47 |

TABLE 3

Synergistic Activity of Compound I and Carbendazim on Several Key Broadleaf Weeds in Cereal Crops

| Application Rate (g/ha) | | KCHSC | | VIOTR | |
|---|---|---|---|---|---|
| Compound I Methyl Ester | Carbendazim | Ob | Ex | Ob | Ex |
| 8.75 | 0 | 65 | — | 53 | — |
| 17.5 | 0 | 71 | — | 58 | — |
| 35 | 0 | 96 | — | 60 | — |
| 0 | 62.5 | 0 | — | 0 | — |
| 8.75 | 62.5 | 62 | 65 | 60 | 53 |
| 17.5 | 62.5 | 86 | 71 | 58 | 58 |
| 35 | 62.5 | 98 | 96 | 65 | 60 |

TABLE 4

Synergistic Activity of Compound I and Chlorothalonil on Several Key Broadleaf Weeds in Cereal Crops

| Application Rate (g/ha) | | KCHSC | | MATCH | | SASKR | | VERPE | | VIOTR | |
|---|---|---|---|---|---|---|---|---|---|---|---|
| Compound I Methyl Ester | Chlorothalonil | Ob | Ex | Ob | Ex | Ob | Ex | Ob | Ex | Ob | Ex |
| 8.75 | 0 | 65 | — | 68 | — | 83 | — | 62 | — | 53 | — |
| 17.5 | 0 | 71 | — | 77 | — | 85 | — | 67 | — | 58 | — |
| 35 | 0 | 96 | — | 85 | — | 88 | — | 78 | — | 60 | — |
| 0 | 250 | 0 | — | 0 | — | 0 | — | 0 | — | 0 | — |
| 8.75 | 250 | 73 | 65 | 78 | 68 | 83 | 83 | 83 | 62 | 68 | 53 |
| 17.5 | 250 | 88 | 71 | 82 | 77 | 87 | 85 | 86 | 67 | 58 | 58 |
| 35 | 250 | 98 | 96 | 88 | 85 | 91 | 88 | 92 | 78 | 63 | 60 |

TABLE 5

Synergistic Activity of Compound I and Chlorothalonil on Several Key Broadleaf Weeds in Cereal Crops

| Application Rate (g/ha) | | KCHSC | | SASKR | |
|---|---|---|---|---|---|
| Compound I TEA Salt | Chlorothalonil | Ob | Ex | Ob | Ex |
| 8.75 | 0 | 40 | | 80 | |
| 17.5 | 0 | 55 | | 84 | |
| 35 | 0 | 65 | | 86 | |
| 0 | 250 | 0 | | 0 | |
| 8.75 | 250 | 53 | 40 | 86 | 80 |
| 17.5 | 250 | 65 | 55 | 86 | 84 |
| 35 | 250 | 86 | 65 | 90 | 86 |

TABLE 6

Synergistic Activity of Compound I and Cyproconazole on Several Key Broadleaf Weeds in Cereal Crops

| Application Rate (g/ha) | | KCHSC | | MATCH | | SASKR | | VERPE | | VIOTR | |
|---|---|---|---|---|---|---|---|---|---|---|---|
| Compound I Methyl Ester | Cyproconazole | Ob | Ex | Ob | Ex | Ob | Ex | Ob | Ex | Ob | Ex |
| 8.75 | 0 | 65 | — | 68 | — | 83 | — | 62 | — | 53 | — |
| 17.5 | 0 | 71 | — | 77 | — | 85 | — | 67 | — | 58 | — |
| 35 | 0 | 96 | — | 85 | — | 88 | — | 78 | — | 60 | — |
| 0 | 19.8 | 0 | — | 0 | — | 0 | — | 0 | — | 0 | — |
| 8.75 | 19.8 | 73 | 65 | 81 | 68 | 88 | 83 | 86 | 62 | 63 | 53 |
| 17.5 | 19.8 | 90 | 71 | 88 | 77 | 88 | 85 | 90 | 67 | 63 | 58 |
| 35 | 19.8 | 95 | 96 | 91 | 85 | 92 | 88 | 89 | 78 | 65 | 60 |

TABLE 7

Synergistic Activity of Compound I and Cyprodinil on Several Key Broadleaf Weeds in Cereal Crops

| Application Rate (g/ha) | | SASKR | |
|---|---|---|---|
| Compound I Methyl Ester | Cyprodinil | Ob | Ex |
| 8.75 | 0 | 83 | — |
| 17.5 | 0 | 85 | — |
| 35 | 0 | 88 | — |
| 0 | 187.5 | 0 | — |
| 8.75 | 187.5 | 85 | 83 |
| 17.5 | 187.5 | 90 | 85 |
| 35 | 187.5 | 88 | 88 |

TABLE 8

Synergistic Activity of Compound I and Epoxiconazole on Several Key Broadleaf Weeds in Cereal Crops

| Application Rate (g/ha) | | KCHSC | | MATCH | | SASKR | | VERPE | | VIOTR | |
|---|---|---|---|---|---|---|---|---|---|---|---|
| Compound I Methyl Ester | Epoxiconazole | Ob | Ex | Ob | Ex | Ob | Ex | Ob | Ex | Ob | Ex |
| 8.75 | 0 | 65 | — | 68 | — | 83 | — | 62 | — | 53 | — |
| 17.5 | 0 | 71 | — | 77 | — | 85 | — | 67 | — | 58 | — |
| 35 | 0 | 96 | — | 85 | — | 88 | — | 78 | — | 60 | — |
| 0 | 31.25 | 0 | — | 0 | — | 0 | — | 0 | — | 0 | — |
| 8.75 | 31.25 | 70 | 65 | 73 | 68 | 91 | 83 | 72 | 62 | 62 | 53 |

TABLE 8-continued

Synergistic Activity of Compound I and Epoxiconazole on Several Key Broadleaf Weeds in Cereal Crops

| Application Rate (g/ha) | | KCHSC | | MATCH | | SASKR | | VERPE | | VIOTR | |
|---|---|---|---|---|---|---|---|---|---|---|---|
| Compound I Methyl Ester | Epoxiconazole | Ob | Ex | Ob | Ex | Ob | Ex | Ob | Ex | Ob | Ex |
| 17.5 | 31.25 | 85 | 71 | 87 | 77 | 88 | 85 | 88 | 67 | 68 | 58 |
| 35 | 31.25 | 96 | 96 | 90 | 85 | 91 | 88 | 93 | 78 | 69 | 60 |

TABLE 9

Synergistic Activity of Compound I and Fenpropidin on Several Key Broadleaf Weeds in Cereal Crops

| Application rate (g/ha) | | AMARE | | CHEAL | | VIOTR | | CIRAR | |
|---|---|---|---|---|---|---|---|---|---|
| Compound I Methyl ester | Fenpropidin | Ob | Ex | Ob | Ex | Ob | Ex | Ob | Ex |
| 17.5 | 0 | 90 | — | 85 | — | 50 | — | 62 | — |
| 0 | 562.5 | 0 | — | 0 | — | 0 | — | 0 | — |
| 17.5 | 562.5 | 100 | 90 | 94 | 85 | 62 | 50 | 78 | 62 |

TABLE 10

Synergistic Activity of Compound I and Flutriafol on Several Key Broadleaf Weeds in Cereal Crops

| Application Rate (g/ha) | | KCHSC | | MATCH | | SASKR | | VIOTR | |
|---|---|---|---|---|---|---|---|---|---|
| Compound I Methyl Ester | Flutriafol | Ob | Ex | Ob | Ex | Ob | Ex | Ob | Ex |
| 8.75 | 0 | 65 | — | 68 | — | 83 | — | 53 | — |
| 17.5 | 0 | 71 | — | 77 | — | 85 | — | 58 | — |
| 35 | 0 | 96 | — | 85 | — | 88 | — | 60 | — |
| 0 | 21.25 | 0 | — | 0 | — | 0 | — | 0 | — |
| 8.75 | 21.25 | 60 | 65 | 70 | 68 | 85 | 83 | 62 | 53 |
| 17.5 | 21.25 | 84 | 71 | 81 | 77 | 91 | 85 | 63 | 58 |
| 35 | 21.5 | 99 | 96 | 81 | 85 | 90 | 88 | 63 | 60 |

TABLE 11

Synergistic Activity of Compound I and Iprodione on Several Key Broadleaf Weeds in Cereal Crops

| Application rate (g/ha) | | AMARE | | VIOTR | | CIRAR | |
|---|---|---|---|---|---|---|---|
| Compound I Methyl ester | Iprodione | Ob | Ex | Ob | Ex | Ob | Ex |
| 17.5 | 0 | 90 | — | 50 | — | 62 | — |
| 0 | 750 | 0 | — | 0 | — | 0 | — |
| 17.5 | 750 | 94 | 90 | 62 | 50 | 68 | 62 |

TABLE 12

Synergistic Activity of Compound I and Kresoxim-methyl on Several Key Broadleaf Weeds in Cereal Crops

| Application Rate (g/ha) | | MATCH | |
|---|---|---|---|
| Compound I Methyl Ester | Kresoxim-methyl | Ob | Ex |
| 8.75 | 0 | 68 | — |
| 17.5 | 0 | 77 | — |
| 35 | 0 | 85 | — |
| 0 | 25 | 0 | — |
| 8.75 | 25 | 79 | 68 |
| 17.5 | 25 | 89 | 77 |
| 35 | 25 | 86 | 85 |

TABLE 13

Synergistic Activity of Compound I and Mancozeb on Several Key Broadleaf Weeds in Cereal Crops

| Application Rate (g/ha) | | KCHSC | | MATCH | | SASKR | | VERPE | | VIOTR | |
|---|---|---|---|---|---|---|---|---|---|---|---|
| Compound I Methyl Ester | Mancozeb | Ob | Ex | Ob | Ex | Ob | Ex | Ob | Ex | Ob | Ex |
| 8.75 | 0 | 65 | — | 68 | — | 83 | — | 62 | — | 53 | — |
| 17.5 | 0 | 71 | — | 77 | — | 85 | — | 67 | — | 58 | — |
| 35 | 0 | 96 | — | 85 | — | 88 | — | 78 | — | 60 | — |
| 0 | 281.25 | 0 | — | 0 | — | 0 | — | 0 | — | 0 | — |

TABLE 13-continued

Synergistic Activity of Compound I and Mancozeb on Several
Key Broadleaf Weeds in Cereal Crops

| Application Rate (g/ha) | | KCHSC | | MATCH | | SASKR | | VERPE | | VIOTR | |
|---|---|---|---|---|---|---|---|---|---|---|---|
| Compound I Methyl Ester | Mancozeb | Ob | Ex | Ob | Ex | Ob | Ex | Ob | Ex | Ob | Ex |
| 8.75 | 281.25 | 77 | 65 | 82 | 68 | 87 | 83 | 82 | 62 | 68 | 53 |
| 17.5 | 281.25 | 86 | 71 | 88 | 77 | 90 | 85 | 82 | 67 | 67 | 58 |
| 35 | 281.25 | 96 | 96 | 90 | 85 | 93 | 88 | 88 | 78 | 64 | 60 |

TABLE 14

Synergistic Activity of Compound I and Mancozeb on Several Key
Broadleaf Weeds in Cereal Crops

| Application Rate (g/ha) | | KCHSC | | VERPE | |
|---|---|---|---|---|---|
| Compound I TEA Salt | Mancozeb | Ob | Ex | Ob | Ex |
| 8.75 | 0 | 40 | | 10 | |
| 17.5 | 0 | 55 | | 40 | |
| 35 | 0 | 65 | | 70 | |
| 0 | 281.25 | 0 | | 0 | |
| 8.75 | 281.25 | 50 | 40 | 30 | 10 |
| 17.5 | 281.25 | 62 | 55 | 72 | 40 |
| 35 | 281.25 | 82 | 65 | 73 | 70 |

TABLE 15

Synergistic Activity of Compound I and Metconazole on Several
Key Broadleaf Weeds in Cereal Crops

| Application Rate (g/ha) | | KCHSC | | MATCH | | SASKR | | VERPE | | VIOTR | |
|---|---|---|---|---|---|---|---|---|---|---|---|
| Compound I Methyl Ester | Metconazole | Ob | Ex | Ob | Ex | Ob | Ex | Ob | Ex | Ob | Ex |
| 8.75 | 0 | 65 | — | 68 | — | 83 | — | 62 | — | 53 | — |
| 17.5 | 0 | 71 | — | 77 | — | 85 | — | 67 | — | 58 | — |
| 35 | 0 | 96 | — | 85 | — | 88 | — | 78 | — | 60 | — |
| 0 | 22.5 | 0 | — | 0 | — | 0 | — | 0 | — | 0 | — |
| 8.75 | 22.5 | 83 | 65 | 72 | 68 | 90 | 83 | 72 | 62 | 65 | 53 |
| 17.5 | 22.5 | 89 | 71 | 82 | 77 | 90 | 85 | 87 | 67 | 68 | 58 |
| 35 | 22.5 | 99 | 96 | 90 | 85 | 91 | 88 | 92 | 78 | 67 | 60 |

TABLE 16

Synergistic Activity of Compound I and Metrafenone on Several
Key Broadleaf Weeds in Cereal Crops

| Application Rate (g/ha) | | MATCH | | SASKR | | VIOTR | |
|---|---|---|---|---|---|---|---|
| Compound I Methyl Ester | Metrafenone | Ob | Ex | Ob | Ex | Ob | Ex |
| 8.75 | 0 | 68 | — | 83 | — | 53 | — |
| 17.5 | 0 | 77 | — | 85 | — | 58 | — |
| 35 | 0 | 85 | — | 88 | — | 60 | — |
| 0 | 37.5 | 0 | — | 0 | — | 0 | — |
| 8.75 | 37.5 | 70 | 68 | 87 | 83 | 60 | 53 |
| 17.5 | 37.5 | 80 | 77 | 87 | 85 | 60 | 58 |

TABLE 17

Synergistic Activity of Compound I and Picoxystrobin on Several Key Broadleaf Weeds in Cereal Crops

| Application rate (g/ha) | | AMARE | | CHEAL | | STEME | | VIOTR | | CIRAR | |
|---|---|---|---|---|---|---|---|---|---|---|---|
| Compound I Methyl ester | Picoxystrobin | Ob | Ex | Ob | Ex | Ob | Ex | Ob | Ex | Ob | Ex |
| 17.5 | 0 | 90 | — | 85 | — | 89 | — | 50 | — | 62 | — |
| 0 | 250 | 0 | — | 0 | — | 0 | — | 0 | — | 0 | — |
| 17.5 | 250 | 100 | 90 | 92 | 85 | 94 | 89 | 62 | 50 | 67 | 62 |

TABLE 18

Synergistic Activity of Compound I and Prochloraz on Several Key Broadleaf Weeds in Cereal Crops

| Application Rate (g/ha) | | MATCH | | SASKR | | VIOTR | |
|---|---|---|---|---|---|---|---|
| Compound I Methyl Ester | Prochloraz | Ob | Ex | ObV | Ex | Ob | Ex |
| 8.75 | 0 | 68 | — | 83 | — | 53 | — |
| 17.5 | 0 | 77 | — | 85 | — | 58 | — |
| 35 | 0 | 85 | — | 88 | — | 60 | — |
| 0 | 101.25 | 0 | — | 0 | — | 0 | — |
| 8.75 | 101.25 | 67 | 68 | 86 | 83 | 58 | 53 |
| 17.5 | 101.25 | 95 | 77 | 91 | 85 | 67 | 58 |
| 35 | 101.25 | 91 | 85 | 92 | 88 | 61 | 60 |

TABLE 19

Synergistic Activity of Compound I and Prochloraz on Several Key Broadleaf Weeds in Cereal Crops

| Application Rate (g/ha) | | KCHSC | | MATCH | | SASKR | | VERPE | | VIOTR | |
|---|---|---|---|---|---|---|---|---|---|---|---|
| Compound I TEA Salt | Prochloraz | Ob | Ex | Ob | Ex | Ob | Ex | Ob | Ex | Ob | Ex |
| 8.75 | 0 | 40 | — | 40 | — | 80 | — | 10 | — | 23 | — |
| 17.5 | 0 | 55 | — | 67 | — | 84 | — | 40 | — | 40 | — |
| 35 | 0 | 65 | — | 73 | — | 86 | — | 70 | — | 47 | — |
| 0 | 101.25 | 0 | — | 0 | — | 0 | — | 0 | — | 0 | — |
| 8.75 | 101.25 | 53 | 40 | 75 | 40 | 86 | 80 | 10 | 10 | 13 | 23 |
| 17.5 | 101.25 | 77 | 55 | 88 | 67 | 89 | 84 | 84 | 40 | 47 | 40 |
| 35 | 101.25 | 93 | 65 | 86 | 73 | 91 | 86 | 93 | 70 | 72 | 47 |

TABLE 20

Synergistic Activity of Compound I and Propioconazole on Several Key Broadleaf Weeds in Cereal Crops

| Application Rate (g/ha) | | KCHSC | | MATCH | | SASKR | | VERPE | | VIOTR | |
|---|---|---|---|---|---|---|---|---|---|---|---|
| Compound I Methyl Ester | Propiconazole | Ob | Ex | Ob | Ex | Ob | Ex | Ob | Ex | Ob | Ex |
| 8.75 | 0 | 65 | — | 68 | — | 83 | — | 62 | — | 53 | — |
| 17.5 | 0 | 71 | — | 77 | — | 85 | — | 67 | — | 58 | — |
| 35 | 0 | 96 | — | 85 | — | 88 | — | 78 | — | 60 | — |
| 0 | 31.25 | 0 | — | 0 | — | 0 | — | 0 | — | 0 | — |
| 8.75 | 31.25 | 72 | 65 | 79 | 68 | 86 | 83 | 62 | 62 | 63 | 53 |
| 17.5 | 31.25 | 87 | 71 | 83 | 77 | 88 | 85 | 77 | 67 | 63 | 58 |
| 35 | 31.25 | 97 | 96 | 90 | 85 | 91 | 88 | 89 | 78 | 67 | 60 |

TABLE 21

Synergistic Activity of Compound I and Proquinazid on Several Key Broadleaf Weeds in Cereal Crops Application Rate (g/ha)

| Compound I Methyl Ester | Proquinazid | MATCH Ob | Ex | VIOTR Ob | Ex |
|---|---|---|---|---|---|
| 8.75 | 0 | 68 | — | 53 | — |
| 17.5 | 0 | 77 | — | 58 | — |
| 35 | 0 | 85 | — | 60 | — |
| 0 | 12.5 | 0 | — | 0 | — |
| 8.75 | 12.5 | 72 | 68 | 58 | 53 |
| 17.5 | 12.5 | 83 | 77 | 63 | 58 |
| 35 | 12.5 | 81 | 85 | 65 | 60 |

TABLE 22

Synergistic Activity of Compound I and Prothioconazole on Several Key Broadleaf Weeds in Cereal Crops Application Rate (g/ha)

| Compound I Methyl Ester | Prothioconazole | KCHSC Ob | Ex | MATCH Ob | Ex | SASKR Ob | Ex | VERPE Ob | Ex | VIOTR Ob | Ex |
|---|---|---|---|---|---|---|---|---|---|---|---|
| 8.75 | 0 | 65 | — | 68 | — | 83 | — | 62 | — | 53 | — |
| 17.5 | 0 | 71 | — | 77 | — | 85 | — | 67 | — | 58 | — |
| 35 | 0 | 96 | — | 85 | — | 88 | — | 78 | — | 60 | — |
| 0 | 50 | 0 | — | 0 | — | 0 | — | 0 | — | 0 | — |
| 8.75 | 50 | 70 | 65 | 70 | 68 | 82 | 83 | 62 | 62 | 65 | 53 |
| 17.5 | 50 | 90 | 71 | 81 | 77 | 89 | 85 | 83 | 67 | 67 | 58 |
| 35 | 50 | 97 | 96 | 87 | 85 | 92 | 88 | 91 | 78 | 73 | 60 |

TABLE 23

Synergistic Activity of Compound I and Pyraclostrobin on Several Key Broadleaf Weeds in Cereal Crops Application Rate (g/ha)

| Compound I Methyl Ester | Pyraclostrobin | KCHSC Ob | Ex | MATCH Ob | Ex | SASKR Ob | Ex | VERPE Ob | Ex | VIOTR Ob | Ex |
|---|---|---|---|---|---|---|---|---|---|---|---|
| 8.75 | 0 | 65 | — | 68 | — | 83 | — | 62 | — | 53 | — |
| 17.5 | 0 | 71 | — | 77 | — | 85 | — | 67 | — | 58 | — |
| 35 | 0 | 96 | — | 85 | — | 88 | — | 78 | — | 60 | — |
| 0 | 18.75 | 0 | — | 0 | — | 0 | — | 0 | — | 0 | — |
| 8.75 | 18.75 | 68 | 65 | 68 | 68 | 84 | 83 | 60 | 62 | 62 | 53 |
| 17.5 | 18.75 | 88 | 71 | 84 | 77 | 88 | 85 | 83 | 67 | 65 | 58 |
| 35 | 18.25 | 97 | 96 | 88 | 85 | 90 | 88 | 89 | 78 | 65 | 60 |

TABLE 24

Synergistic Activity of Compound I and Quinoxyfen on Several Key Broadleaf Weeds in Cereal Crops Application Rate (g/ha)

| Compound I Methyl Ester | Quinoxyfen | KCHSC Ob | Ex | VIOTR Ob | Ex |
|---|---|---|---|---|---|
| 8.75 | 0 | 65 | — | 53 | — |
| 17.5 | 0 | 71 | — | 58 | — |
| 35 | 0 | 96 | — | 60 | — |
| 0 | 37.5 | 0 | — | 0 | — |
| 8.75 | 37.5 | 63 | 65 | 65 | 53 |
| 17.5 | 37.5 | 75 | 71 | 65 | 58 |
| 35 | 37.5 | 100 | 96 | 66 | 60 |

TABLE 25

Synergistic Activity of Compound I and Quinoxyfen on Several Key Broadleaf Weeds in Cereal Crops Application Rate (g/ha)

| Compound I TEA Salt | Quinoxyfen | KCHSC Ob | Ex | MATCH Ob | Ex | SASKR Ob | Ex | VERPE Ob | Ex | VIOTR Ob | Ex |
|---|---|---|---|---|---|---|---|---|---|---|---|
| 8.75 | 0 | 40 | | 40 | | 80 | | 10 | | 23 | |
| 17.5 | 0 | 55 | | 67 | | 84 | | 40 | | 40 | |

TABLE 25-continued

Synergistic Activity of Compound I and Quinoxyfen
on Several Key Broadleaf Weeds in Cereal Crops Application Rate (g/ha)

| Compound I TEA Salt | Quinoxyfen | KCHSC Ob | Ex | MATCH Ob | Ex | SASKR Ob | Ex | VERPE Ob | Ex | VIOTR Ob | Ex |
|---|---|---|---|---|---|---|---|---|---|---|---|
| 35 | 0 | 65 | | 73 | | 86 | | 70 | | 47 | |
| 0 | 37.5 | 0 | | 0 | | 0 | | 0 | | 0 | |
| 8.75 | 37.5 | 47 | 40 | 68 | 40 | 85 | 80 | 20 | 10 | 33 | 23 |
| 17.5 | 37.5 | 60 | 55 | 80 | 67 | 91 | 84 | 84 | 40 | 72 | 40 |
| 35 | 37.5 | 83 | 65 | 80 | 73 | 92 | 86 | 91 | 70 | 78 | 47 |

TABLE 26

Synergistic Activity of Compound I and Spiroxamine on
Several Key Broadleaf Weeds in Cereal Crops Application Rate (g/ha)

| Compound I Methyl Ester | Spiroxamine | KCHSC Ob | Ex | MATCH Ob | Ex | VIOTR Ob | Ex |
|---|---|---|---|---|---|---|---|
| 8.75 | 0 | 65 | — | 68 | — | 53 | — |
| 17.5 | 0 | 71 | — | 77 | — | 58 | — |
| 35 | 0 | 96 | — | 85 | — | 60 | — |
| 0 | 180 | 0 | — | 0 | — | 0 | — |
| 8.75 | 180 | 60 | 65 | 73 | 68 | 65 | 53 |
| 17.5 | 180 | 84 | 71 | 81 | 77 | 65 | 58 |
| 35 | 180 | 98 | 96 | 77 | 85 | 67 | 60 |

TABLE 27

Synergistic Activity of Compound I and Tebuconazole on Several
Key Broadleaf Weeds in Cereal Crops Application Rate (g/ha)

| Compound I Methyl Ester | Tebuconazole | KCHSC Ob | Ex | MATCH Ob | Ex | SASKR Ob | Ex | VERPE Ob | Ex | VIOTR Ob | Ex |
|---|---|---|---|---|---|---|---|---|---|---|---|
| 8.75 | 0 | 65 | — | 68 | — | 83 | — | 62 | — | 53 | — |
| 17.5 | 0 | 71 | — | 77 | — | 85 | — | 67 | — | 58 | — |
| 35 | 0 | 96 | — | 85 | — | 88 | — | 78 | — | 60 | — |
| 0 | 62.5 | — | | — | | — | | — | | — | |
| 0 | 250 | — | | — | | — | | — | | — | |
| 8.75 | 62.5 | 78 | 65 | 72 | 68 | 84 | 83 | 60 | 62 | 58 | 53 |
| 17.5 | 62.5 | 85 | 71 | 82 | 77 | 91 | 85 | 84 | 67 | 65 | 58 |
| 35 | 62.5 | 97 | 96 | 89 | 85 | 91 | 88 | 87 | 78 | 67 | 60 |
| 35 | 250 | 99 | 96 | 95 | 85 | 92 | 88 | 86 | 78 | 55 | 60 |

TABLE 28

Synergistic Activity of Compound I and Tebuconazole on
Several Key Broadleaf Weeds in Cereal Crops Application Rate (g/ha)

| Compound I TEA Salt | Tebuconazole | KCHSC Ob | Ex | MATCH Ob | Ex | SASKR Ob | Ex | VERPE Ob | Ex | VIOTR Ob | Ex |
|---|---|---|---|---|---|---|---|---|---|---|---|
| 8.75 | 0 | 40 | | 40 | | 80 | | 10 | | 23 | |
| 17.5 | 0 | 55 | | 67 | | 84 | | 40 | | 40 | |
| 35 | 0 | 65 | | 73 | | 86 | | 70 | | 47 | |
| 0 | 31.25 | 0 | | 0 | | 0 | | 0 | | 0 | |
| 8.75 | 31.25 | 50 | 40 | 66 | 40 | 86 | 80 | 23 | 10 | 50 | 23 |
| 17.5 | 31.25 | 72 | 55 | 62 | 67 | 87 | 84 | 38 | 40 | 27 | 40 |
| 35 | 31.25 | 89 | 65 | 72 | 73 | 89 | 86 | 68 | 70 | 43 | 47 |

TABLE 29

Synergistic Activity of Compound I and Tetraconazole on
Several Key Broadleaf Weeds in Cereal Crops Application rate (g/ha)

| Compound I Methyl ester | Tetraconazole | AMARE Ob | Ex | CHEAL Ob | Ex | STEME Ob | Ex | VIOTR Ob | Ex | CIRAR Ob | Ex |
|---|---|---|---|---|---|---|---|---|---|---|---|
| 17.5 | 0 | 90 | — | 85 | — | 89 | — | 50 | — | 62 | — |
| 0 | 125 | 0 | — | 0 | — | 0 | — | 0 | — | 0 | — |
| 17.5 | 125 | 97 | 90 | 93 | 85 | 98 | 89 | 65 | 50 | 79 | 62 |

TABLE 30

Synergistic Activity of Compound I and Thiophanate-methyl on Several Key Broadleaf Weeds in Cereal Crops

| Application rate (g/ha) | | AMARE | | CHEAL | | STEME | | VIOTR | | CIRAR | |
|---|---|---|---|---|---|---|---|---|---|---|---|
| Compound I Methyl ester | Thiophanate-methyl | Ob | Ex | Ob | Ex | Ob | Ex | Ob | Ex | Ob | Ex |
| 17.5 | 0 | 90 | — | 85 | — | 89 | — | 50 | — | 62 | — |
| 0 | 750 | 0 | — | 0 | — | 0 | — | 0 | — | 0 | — |
| 17.5 | 750 | 98 | 90 | 92 | 85 | 98 | 89 | 67 | 50 | 77 | 62 |

TABLE 31

Synergistic Activity of Compound I and Trifloxystrobin on Several Key Broadleaf Weeds in Cereal Crops

| Application Rate (g/ha) | | KCHSC | | MATCH | | SASKR | | VERPE | | VIOTR | |
|---|---|---|---|---|---|---|---|---|---|---|---|
| Compound I Methyl Ester | Trifloxystrobin | Ob | Ex | Ob | Ex | Ob | Ex | Ob | Ex | Ob | Ex |
| 8.75 | 0 | 65 | — | 68 | — | 83 | — | 62 | — | 53 | — |
| 17.5 | 0 | 71 | — | 77 | — | 85 | — | 67 | — | 58 | — |
| 35 | 0 | 96 | — | 85 | — | 88 | — | 78 | — | 60 | — |
| 0 | 62.5 | 0 | — | 0 | — | 0 | — | 0 | — | 0 | — |
| 8.75 | 62.5 | 70 | 65 | 75 | 68 | 86 | 83 | 80 | 62 | 55 | 53 |
| 17.5 | 62.5 | 86 | 71 | 81 | 77 | 88 | 85 | 82 | 67 | 62 | 58 |
| 35 | 62.5 | 97 | 96 | 88 | 85 | 92 | 88 | 90 | 78 | 63 | 60 |

TABLE 32

Synergistic Activity of Compound I and XR-777 on Several Key Broadleaf Weeds in Cereal Crops

| Application Rate (g/ha) | | KCHSC | | MATCH | | SASKR | | VIOTR | |
|---|---|---|---|---|---|---|---|---|---|
| Compound I Methyl Ester | Compound II | Ob | Ex | Ob | Ex | Ob | Ex | Ob | Ex |
| 8.75 | 0 | 65 | — | 68 | — | 83 | — | 53 | — |
| 17.5 | 0 | 71 | — | 77 | — | 85 | — | 58 | — |
| 35 | 0 | 96 | — | 85 | — | 88 | — | 60 | — |
| 0 | 40.5 | 0 | — | 0 | — | 0 | — | 0 | — |
| 8.75 | 40.5 | 62 | 65 | 72 | 68 | 86 | 83 | 62 | 53 |
| 17.5 | 40.5 | 89 | 71 | 97 | 77 | 91 | 85 | 63 | 58 |
| 35 | 40.5 | 97 | 96 | 88 | 85 | 87 | 88 | 65 | 60 |

TABLE 33

Safening Activity of Herbicidal Compositions on Wheat

| Application Rate (g/ha) | | | TRZAS | | HORVS | | KCHSC | | MATCH | | SASKR | | VERPE | | VIOTR | |
|---|---|---|---|---|---|---|---|---|---|---|---|---|---|---|---|---|
| Compound I Methyl Ester | Cyproconazole | Cloquintocet-mexyl | Ob | Ex | Ob | Ex | Ob | Ex | Ob | Ex | Ob | Ex | Ob | Ex | Ob | Ex |
| 35 | 0 | 0 | 50 | — | 37 | — | 96 | — | 85 | — | 88 | — | 78 | — | 60 | — |
| 0 | 0 | 8.8 | 0 | — | 0 | — | 0 | — | 0 | — | 0 | — | 0 | — | 0 | — |
| 0 | 0 | 35 | 0 | — | 0 | — | 0 | — | 0 | — | 0 | — | 0 | — | 0 | — |
| 35 | 0 | 8.8 | 0 | — | 0 | — | 100 | — | 86 | — | 89 | — | 78 | — | 43 | — |
| 35 | 0 | 35 | 0 | — | 0 | — | 100 | — | 86 | — | 87 | — | 76 | — | 41 | — |
| 35 | 19.8 | 0 | 53 | 50 | 36 | 37 | 95 | 96 | 91 | 85 | 92 | 88 | 89 | 78 | 65 | 60 |
| 35 | 19.8 | 8.8 | 0 | 50 | 0 | 37 | 100 | 96 | 96 | 85 | 90 | 88 | 94 | 78 | 53 | 60 |
| 35 | 19.8 | 35 | 0 | 50 | 0 | 37 | 100 | 96 | 95 | 85 | 91 | 88 | 93 | 78 | 57 | 60 |

TABLE 34

Safening Activity of Herbicidal Compositions on Wheat and Barley

| Application Rate (g/ha) | | | TRZAS | | HORVS | | KCHSC | | MATCH | | SASKR | | VERPE | | VIOTR | |
|---|---|---|---|---|---|---|---|---|---|---|---|---|---|---|---|---|
| Compound I Methyl Ester | Mancozeb | Cloquintocet-mexyl | Ob | Ex | Ob | Ex | Ob | Ex | Ob | Ex | Ob | Ex | Ob | Ex | Ob | Ex |
| 35 | 0 | 0 | 50 | — | 37 | — | 96 | — | 85 | — | 88 | — | 78 | — | 60 | — |
| 0 | 0 | 8.8 | 0 | — | 0 | — | 0 | — | 0 | — | 0 | — | 0 | — | 0 | — |
| 0 | 0 | 35 | 0 | — | 0 | — | 0 | — | 0 | — | 0 | — | 0 | — | 0 | — |
| 35 | 0 | 8.8 | 0 | — | 0 | — | 100 | — | 86 | — | 89 | — | 78 | — | 43 | — |
| 35 | 0 | 35 | 0 | — | 0 | — | 100 | — | 86 | — | 87 | — | 76 | — | 41 | — |
| 35 | 281.25 | 0 | 53 | 50 | 43 | 37 | 96 | 96 | 90 | 85 | 93 | 88 | 88 | 78 | 64 | 60 |
| 35 | 281.25 | 8.8 | 0 | 50 | 0 | 37 | 100 | 96 | 91 | 85 | 89 | 88 | 94 | 78 | 55 | 60 |
| 35 | 281.25 | 35 | 0 | 50 | 0 | 37 | 100 | 96 | 93 | 85 | 89 | 88 | 93 | 78 | 53 | 60 |

TABLE 35

Safening Activity of Herbicidal Compositions on Wheat and Barley

| Application Rate (g/ha) | | | TRZAS | | HORVS | | KCHSC | | MATCH | | SASKR | | VERPE | | VIOTR | |
|---|---|---|---|---|---|---|---|---|---|---|---|---|---|---|---|---|
| Compound I Methyl Ester | Metconazole | Cloquintocet-mexyl | Ob | Ex | Ob | Ex | Ob | Ex | Ob | Ex | Ob | Ex | Ob | Ex | Ob | Ex |
| 35 | 0 | 0 | 50 | — | 37 | — | 96 | — | 85 | — | 88 | — | 78 | — | 60 | — |
| 0 | 0 | 8.8 | 0 | — | 0 | — | 0 | — | 0 | — | 0 | — | 0 | — | 0 | — |
| 0 | 0 | 35 | 0 | — | 0 | — | 0 | — | 0 | — | 0 | — | 0 | — | 0 | — |
| 35 | 0 | 8.8 | 0 | — | 0 | — | 100 | — | 86 | — | 89 | — | 78 | — | 43 | — |
| 35 | 0 | 35 | 0 | — | 0 | — | 100 | — | 86 | — | 87 | — | 76 | — | 41 | — |
| 35 | 22.5 | 0 | 60 | 50 | 48 | 37 | 99 | 96 | 90 | 85 | 91 | 88 | 92 | 78 | 67 | 60 |
| 35 | 22.5 | 8.8 | 0 | 50 | 0 | 37 | 100 | 96 | 94 | 85 | 91 | 88 | 93 | 78 | 50 | 60 |
| 35 | 22.5 | 35 | 0 | 50 | 0 | 37 | 100 | 96 | 95 | 85 | 91 | 88 | 93 | 78 | 57 | 60 |

TABLE 36

Safening Activity of Herbicidal Compositions on Wheat and Barley

| Application Rate (g/ha) | | | TRZAS | | HORVS | | KCHSC | | MATCH | | SASKR | | VERPE | | VIOTR | |
|---|---|---|---|---|---|---|---|---|---|---|---|---|---|---|---|---|
| Compound I Methyl Ester | Prochloraz | Cloquintocet-mexyl | Ob | Ex | Ob | Ex | Ob | Ex | Ob | Ex | Ob | Ex | Ob | Ex | Ob | Ex |
| 35 | 0 | 0 | 50 | — | 37 | — | 96 | — | 85 | — | 88 | — | 78 | — | 60 | — |
| 0 | 0 | 8.8 | 0 | — | 0 | — | 0 | — | 0 | — | 0 | — | 0 | — | 0 | — |
| 0 | 0 | 35 | 0 | — | 0 | — | 0 | — | 0 | — | 0 | — | 0 | — | 0 | — |
| 35 | 0 | 8.8 | 0 | — | 0 | — | 100 | — | 86 | — | 89 | — | 78 | — | 43 | — |
| 35 | 0 | 35 | 0 | — | 0 | — | 100 | — | 86 | — | 87 | — | 76 | — | 41 | — |
| 35 | 101.25 | 0 | 54 | 50 | 48 | 37 | 99 | 96 | 91 | 85 | 92 | 88 | 63 | 78 | 61 | 60 |
| 35 | 101.25 | 8.8 | 0 | 50 | 0 | 37 |  | 96 | 80 | 85 | 88 | 88 | 70 | 78 | 50 | 60 |
| 35 | 101.25 | 35 | 0 | 50 | 0 | 37 |  | 96 | 87 | 85 | 87 | 88 | 65 | 78 | 47 | 60 |

TABLE 37

Safening Activity of Herbicidal Compositions on Wheat and Barley

| Application Rate (g/ha) | | | TRZAS | | HORVS | | KCHSC | | MATCH | | SASKR | | VERPE | | VIOTR | |
|---|---|---|---|---|---|---|---|---|---|---|---|---|---|---|---|---|
| Compound I Methyl Ester | Tebuconazole | Cloquintocet-mexyl | Ob | Ex | Ob | Ex | Ob | Ex | Ob | Ex | Ob | Ex | Ob | Ex | Ob | Ex |
| 35 | 0 | 0 | 50 | — | 37 | — | 96 | — | 85 | — | 88 | — | 78 | — | 60 | — |
| 0 | 0 | 2.2 | 0 | — | 0 | — | 0 | — | 0 | — | 0 | — | 0 | — | 0 | — |

TABLE 37-continued

Safening Activity of Herbicidal Compositions on Wheat and Barley

Application Rate (g/ha)

| Compound I Methyl Ester | Tebuconazole | Cloquintocet-mexyl | TRZAS Ob | Ex | HORVS Ob | Ex | KCHSC Ob | Ex | MATCH Ob | Ex | SASKR Ob | Ex | VERPE Ob | Ex | VIOTR Ob | Ex |
|---|---|---|---|---|---|---|---|---|---|---|---|---|---|---|---|---|
| 0 | 0 | 4.4 | 0 | — | 0 | — | 0 | — | 0 | — | 0 | — | 0 | — | 0 | — |
| 0 | 0 | 8.8 | 0 | — | 0 | — | 0 | — | 0 | — | 0 | — | 0 | — | 0 | — |
| 0 | 0 | 35 | 0 | — | 0 | — | 0 | — | 0 | — | 0 | — | 0 | — | 0 | — |
| 35 | 0 | 2.2 | 0 | 50 | 0 | 37 | 100 | 96 | 90 | 85 | 91 | 88 | 78 | 78 | 50 | 60 |
| 35 | 0 | 4.4 | 0 | 50 | 0 | 37 | 100 | 96 | 87 | 85 | 89 | 88 | 85 | 78 | 53 | 60 |
| 35 | 0 | 8.8 | 0 | 50 | 0 | 37 | 100 | 96 | 86 | 85 | 89 | 88 | 78 | 78 | 43 | 60 |
| 35 | 0 | 35 | 0 | 50 | 0 | 37 | 100 | 96 | 86 | 85 | 87 | 88 | 76 | 78 | 41 | 60 |
| 0 | 62.5 | 0 | 0 | — | 0 | — | 0 | — | 0 | — | 0 | — | 0 | — | 0 | — |
| 35 | 62.5 | 0 | 63 | 50 | 56 | 37 | 97 | 96 | 89 | 85 | 91 | 88 | 87 | 78 | 67 | 60 |
| 35 | 62.5 | 8.8 | 0 | 50 | 0 | 37 | 100 | 96 | 96 | 85 | 94 | 88 | 94 | 78 | 50 | 60 |
| 35 | 62.5 | 35 | 0 | 50 | 0 | 37 | 100 | 96 | 94 | 85 | 95 | 88 | 95 | 78 | 60 | 60 |
| 0 | 250 | 0 | 0 | — | 0 | — | 0 | — | 0 | — | 0 | — | 0 | — | 0 | — |
| 35 | 250 | 0 | 65 | 50 | 67 | 37 | 99 | 96 | 95 | 85 | 92 | 88 | 86 | 78 | 55 | 60 |
| 35 | 250 | 2.2 | 0 | 50 | 0 | 37 | 98 | 96 | 95 | 85 | 92 | 88 | 72 | 78 | 58 | 60 |
| 35 | 250 | 4.4 | 0 | 50 | 0 | 37 | 100 | 96 | 87 | 85 | 92 | 88 | 73 | 78 | 52 | 60 |
| 35 | 250 | 8.8 | 0 | 50 | 0 | 37 | 100 | 96 | 96 | 85 | 94 | 88 | 70 | 78 | 57 | 60 |

TABLE 38

Safening Activity of Herbicidal Compositions on Wheat and Barley

Application Rate (g/ha)

| Compound I Acid | Azoxystrobin | Cloquintocet | TRZAS Ob | Ex | HORVS Ob | Ex | KCHSC Ob | Ex | MATCH Ob | Ex | SASKR Ob | Ex | VERPE Ob | Ex |
|---|---|---|---|---|---|---|---|---|---|---|---|---|---|---|
| 35 | 0 | 0 | 22 | — | 15 | — | 98 | — | 87 | — | 89 | — | 72 | — |
| 0 | 0 | 2.2 | 0 | — | 0 | — | 0 | — | 0 | — | 0 | — | 0 | — |
| 0 | 0 | 4.4 | 0 | — | 0 | — | 0 | — | 0 | — | 0 | — | 0 | — |
| 0 | 0 | 8.75 | 0 | — | 0 | — | 0 | — | 0 | — | 0 | — | 0 | — |
| 35 | 0 | 2.2 | 0 | 22 | 0 | 15 | 100 | 98 | 84 | 87 | 90 | 89 | 73 | 72 |
| 35 | 0 | 4.4 | 0 | 22 | 0 | 15 | 99 | 98 | 68 | 87 | 91 | 89 | 70 | 72 |
| 35 | 0 | 8.75 | 0 | 22 | 0 | 15 | 98 | 98 | 77 | 87 | 89 | 89 | 77 | 72 |
| 0 | 250 | 0 | 0 | — | 0 | — | 0 | — | 0 | — | 0 | — | 0 | — |
| 35 | 250 | 0 | 38 | 22 | 15 | 15 | 97 | 98 | 87 | 87 | 88 | 89 | 72 | 72 |
| 35 | 250 | 2.2 | 3 | 22 | 0 | 15 | 99 | 98 | 95 | 87 | 90 | 89 | 68 | 72 |
| 35 | 250 | 4.4 | 3 | 22 | 0 | 15 | 100 | 98 | 91 | 87 | 91 | 89 | 75 | 72 |
| 35 | 250 | 8.75 | 0 | 22 | 0 | 15 | 100 | 98 | 87 | 87 | 92 | 89 | 76 | 72 |

TABLE 39

Safening Activity of Herbicidal Compositions on Wheat and Barley

Application Rate (g/ha)

| Compound I Acid | Tebuconazole | Cloquintocet | TRZAS Ob | Ex | HORVS Ob | Ex | KCHSC Ob | Ex | MATCH Ob | Ex | SASKR Ob | Ex | VERPE Ob | Ex | VIOTR Ob | Ex |
|---|---|---|---|---|---|---|---|---|---|---|---|---|---|---|---|---|
| 35 | 0 | 0 | 22 | — | 15 | — | 98 | — | 87 | — | 89 | — | 72 | — | 60 | — |
| 0 | 0 | 2.2 | 0 | — | 0 | — | 0 | — | 0 | — | 0 | — | 0 | — | 0 | — |
| 0 | 0 | 4.4 | 0 | — | 0 | — | 0 | — | 0 | — | 0 | — | 0 | — | 0 | — |
| 0 | 0 | 8.75 | 0 | — | 0 | — | 0 | — | 0 | — | 0 | — | 0 | — | 0 | — |
| 35 | 0 | 2.2 | 0 | 22 | 0 | 15 | 100 | 98 | 84 | 87 | 90 | 89 | 73 | 72 | 57 | 60 |
| 35 | 0 | 4.4 | 0 | 22 | 0 | 15 | 99 | 98 | 68 | 87 | 91 | 89 | 70 | 72 | 55 | 60 |
| 35 | 0 | 8.75 | 0 | 22 | 0 | 15 | 98 | 98 | 77 | 87 | 89 | 89 | 77 | 72 | 52 | 60 |
| 0 | 250 | 0 | 0 | — | 0 | — | 0 | — | 0 | — | 0 | — | 0 | — | 0 | — |
| 35 | 250 | 0 | 72 | 22 | 67 | 15 | 99 | 98 | 98 | 87 | 93 | 89 | 86 | 72 | 60 | 60 |
| 35 | 250 | 2.2 | 7 | 22 | 5 | 15 | 97 | 98 | 94 | 87 | 94 | 89 | 85 | 72 | 62 | 60 |

TABLE 39-continued

Safening Activity of Herbicidal Compositions on Wheat and Barley

| Application Rate (g/ha) | | | TRZAS | | HORVS | | KCHSC | | MATCH | | SASKR | | VERPE | | VIOTR | |
|---|---|---|---|---|---|---|---|---|---|---|---|---|---|---|---|---|
| Compound I Acid | Tebuconazole | Cloquintocet | Ob | Ex | Ob | Ex | Ob | Ex | Ob | Ex | Ob | Ex | Ob | Ex | Ob | Ex |
| 35 | 250 | 4.4 | 7 | 22 | 0 | 15 | 100 | 98 | 98 | 87 | 95 | 89 | 85 | 72 | 63 | 60 |
| 35 | 250 | 8.75 | 3 | 22 | 0 | 15 | 97 | 98 | 95 | 87 | 90 | 89 | 91 | 72 | 50 | 60 |

TRZAS = *Triticum aestivum*, wheat
HORVS = *Hordeum vulgare*, barley
MATCH = *Matricaria chamomila*, scented mayweed
VERPE = *Veronica persica*, bird's-eye speedwell
VIOTR = *Viola tricolor*, wild pansy
KCHSC = *Kochia scoparia*, kochia
SASKR = *Salsola iberica*, Russian thistle
AMARE = *Amaranthus retroflexus*, Redroot pigweed
CHEAL = *Chenopodium album*, lamb's-quarters
STEME = *Stellaria media*, chickweed
CIRAR = *Cirsium arvense*, Canada thistle

What is claimed is:

1. A synergistic herbicide/fungicide mixture comprising an herbicidally effective amount of (a) a pyridine carboxylic acid herbicide of the formula (I)

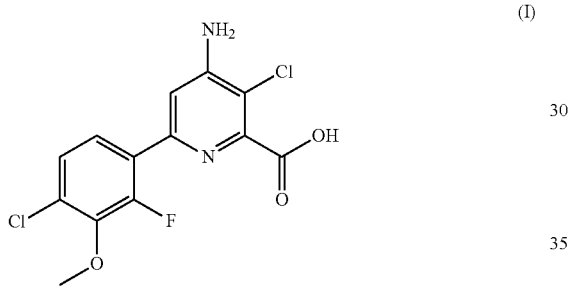

(I)

or an agriculturally acceptable salt, ester, or amide thereof, and (b) a fungicide selected from the group consisting of azoxystrobin, carbendazim, chlorothalonil, cyproconazole, cyprodinil, epoxiconazole, fenpropidin, flutriafol, iprodione, kresoxim-methyl, mancozeb, metconazole, metrafenone, picoxystrobin, prochloraz, propiconazole, proquinazid, prothioconazole, pyraclostrobin, quinoxyfen, spiroxamine, tebuconazole, tetraconazole, thiophanate-methyl, trifloxystrobin, and a picolinamide fungicide of formula (II)

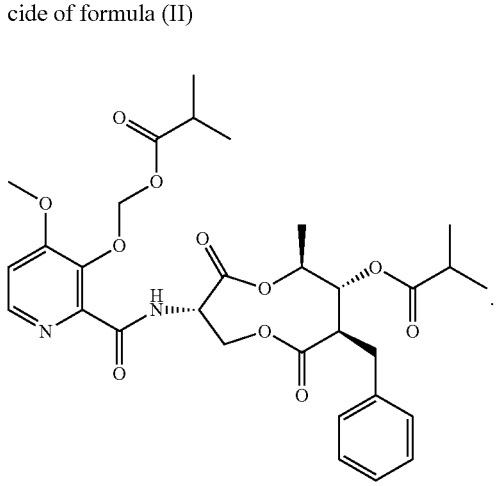

(II)

wherein:
when the fungicide is azoxystrobin, the weight ratio of the pyridine carboxylic acid herbicide component to the fungicide component ranges from 35:62.5 to 35:250;
when the fungicide is carbendazim, the weight ratio of the pyridine carboxylic acid herbicide component to the fungicide component ranges from 35:62.5 to 8.75:62.5;
when the fungicide is chlorothalonil, the weight ratio of the pyridine carboxylic acid herbicide component to the fungicide component ranges from 35:250 to 8.75:250;
when the fungicide is cyproconazole, the weight ratio of the pyridine carboxylic acid herbicide component to the fungicide component ranges from 35:19.8 to 8.75:19.8;
when the fungicide is cyprodinil, the weight ratio of the pyridine carboxylic acid herbicide component to the fungicide component ranges from 35:187.5 to 8.75:187.5;
when the fungicide is epoxiconazole, the weight ratio of the pyridine carboxylic acid herbicide component to the fungicide component ranges from 35:31.25 to 8.75:31.25;
when the fungicide is flutriafol, the weight ratio of the pyridine carboxylic acid herbicide component to the fungicide component ranges from 35:21.5 to 8.75:21.25;
when the fungicide is kresoxim-methyl, the weight ratio of the pyridine carboxylic acid herbicide component to the fungicide component ranges from 35:25 to 8.75:25;
when the fungicide is mancozeb, the weight ratio of the pyridine carboxylic acid herbicide component to the fungicide component ranges from 35:281.25 to 8.75:281.25;
when the fungicide is metconazole, the weight ratio of the pyridine carboxylic acid herbicide component to the fungicide component ranges from 35:22.5 to 8.75:22.5;
when the fungicide is metrafenone, the weight ratio of the pyridine carboxylic acid herbicide component to the fungicide component ranges from 17.5:37.5 to 8.75:37.5;

when the fungicide is prochloraz, the weight ratio of the pyridine carboxylic acid herbicide component to the fungicide component ranges from 35:101.25 to 8.75:101.25;

when the fungicide is propiconazole, the weight ratio of the pyridine carboxylic acid herbicide component to the fungicide component ranges from 35:31.25 to 8.75:31.25;

when the fungicide is proquinazid, the weight ratio of the pyridine carboxylic acid herbicide component to the fungicide component ranges from 35:12.5 to 8.75:12.5;

when the fungicide is prothioconazole, the weight ratio of the pyridine carboxylic acid herbicide component to the fungicide component ranges from 35:50 to 8.75:50;

when the fungicide is pyraclostrobin, the weight ratio of the pyridine carboxylic acid herbicide component to the fungicide component ranges from 35:18.25 to 8.75:18.75;

when the fungicide is quinoxyfen, the weight ratio of the pyridine carboxylic acid herbicide component to the fungicide component ranges from 35:37.5 to 8.75:37.5;

when the fungicide is spiroxamine, the weight ratio of the pyridine carboxylic acid herbicide component to the fungicide component ranges from 35:180 to 8.75:180;

when the fungicide is tebuconazole, the weight ratio of the pyridine carboxylic acid herbicide component to the fungicide component ranges from 35:31.25 to 35:250;

when the fungicide is trifloxystrobin, the weight ratio of the pyridine carboxylic acid herbicide component to the fungicide component ranges from 35:62.5 to 8.75:62.5;

when the fungicide is the picolinamide fungicide of formula (II), the weight ratio of the pyridine carboxylic acid herbicide component to the fungicide component ranges from 35:40.5 to 8.75:40.5;

when the fungicide is fenpropidin, the weight ratio of the pyridine carboxylic acid herbicide component to the fungicide component is 17.5:562.5;

when the fungicide is iprodione, the weight ratio of the pyridine carboxylic acid herbicide component to the fungicide component is 17.5:750;

when the fungicide is picoxystrobin, the weight ratio of the pyridine carboxylic acid herbicide component to the fungicide component is 17.5:250;

when the fungicide is tetraconazole, the weight ratio of the pyridine carboxylic acid herbicide component to the fungicide component is 17.5:125; and when the fungicide is thiophanate-methyl, the weight ratio of the pyridine carboxylic acid herbicide component to the fungicide component is 17.5:750.

2. The synergistic mixture of claim 1 additionally comprising an herbicide safener.

3. The synergistic mixture of claim 2 in which the herbicide safener is cloquintocet-mexyl.

4. An herbicidal composition comprising an herbicidally effective amount of the synergistic herbicide/fungicide mixture of claim 1 and an agriculturally acceptable adjuvant or carrier.

5. The synergistic mixture of claim 1, wherein the fungicide is azoxystrobin.

6. The synergistic mixture of claim 1, wherein the fungicide is carbendazim.

7. The synergistic mixture of claim 1, wherein the fungicide is chlorothalonil.

8. The synergistic mixture of claim 1, wherein the fungicide is cyproconazole.

9. The synergistic mixture of claim 1, wherein the fungicide is cyprodinil.

10. The synergistic mixture of claim 1, wherein the fungicide is epoxiconazole.

11. The synergistic mixture of claim 1, wherein the fungicide is flutriafol.

12. The synergistic mixture of claim 1, wherein the fungicide is kresoxim-methyl.

13. The synergistic mixture of claim 1, wherein the fungicide is mancozeb.

14. The synergistic mixture of claim 1, wherein the fungicide is metconazole.

15. The synergistic mixture of claim 1, wherein the fungicide is metrafenone.

16. The synergistic mixture of claim 1, wherein the fungicide is prochloraz.

17. The synergistic mixture of claim 1, wherein the fungicide is propiconazole.

18. The synergistic mixture of claim 1, wherein the fungicide is proquinazid.

19. The synergistic mixture of claim 1, wherein the fungicide is prothioconazole.

20. The synergistic mixture of claim 1, wherein the fungicide is pyraclostrobin.

21. The synergistic mixture of claim 1, wherein the fungicide is quinoxyfen.

22. The synergistic mixture of claim 1, wherein the fungicide is spiroxamine.

23. The synergistic mixture of claim 1, wherein the fungicide is tebuconazol.

24. The synergistic mixture of claim 1, wherein the fungicide is trifloxystrobin.

25. The synergistic mixture of claim 1, wherein the fungicide is the picolinamide fungicide of formula (II).

26. The synergistic mixture of claim 1, wherein the fungicide is fenpropidin.

27. The synergistic mixture of claim 1, wherein the fungicide is iprodione.

28. The synergistic mixture of claim 1, wherein the fungicide is picoxystrobin.

29. The synergistic mixture of claim 1, wherein the fungicide is tetraconazole.

30. The synergistic mixture of claim 1, wherein the fungicide is thiophanate-methyl.

31. A method of controlling undesirable vegetation which comprises contacting the vegetation or the locus thereof with or applying to the soil or water to prevent reduce the emergence or growth of vegetation an herbicidally effective amount of a synergistic herbicide/fungicide mixture comprising an herbicidally effective amount of (a) a pyridine carboxylic acid herbicide of the formula (I)

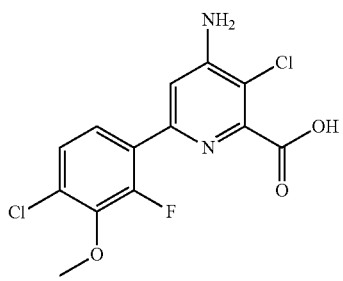

(I)

or an agriculturally acceptable salt, ester, or amide thereof, and (b) a fungicide selected from the group consisting of azoxystrobin, carbendazim, chlorothalonil, cyproconazole, cyprodinil, epoxiconazole, fenpropidin, flutriafol, iprodione, kresoxim-methyl, mancozeb, metconazole, metrafenone, picoxystrobin, prochloraz, propiconazole, proquinazid, prothioconazole, pyraclostrobin, quinoxyfen, spiroxamine, tebuconazole, tetraconazole, thiophanate-methyl, trifloxystrobin, and a picolinamide fungicide of formula (II)

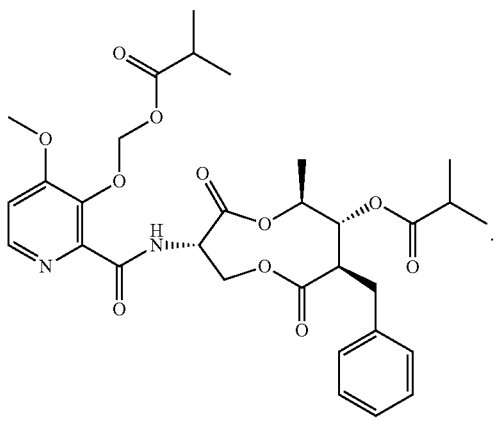

(II)

wherein:
  when the fungicide is azoxystrobin, the weight ratio of the pyridine carboxylic acid herbicide component to the fungicide component ranges from 35:62.5 to 35:250;
  when the fungicide is carbendazim, the weight ratio of the pyridine carboxylic acid herbicide component to the fungicide component ranges from 35:62.5 to 8.75:62.5;
  when the fungicide is chlorothalonil, the weight ratio of the pyridine carboxylic acid herbicide component to the fungicide component ranges from 35:250 to 8.75:250;
  when the fungicide is cyproconazole, the weight ratio of the pyridine carboxylic acid herbicide component to the fungicide component ranges from 35:19.8 to 8.75:19.8;
  when the fungicide is cyprodinil, the weight ratio of the pyridine carboxylic acid herbicide component to the fungicide component ranges from 35:187.5 to 8.75:187.5;
  when the fungicide is epoxiconazole, the weight ratio of the pyridine carboxylic acid herbicide component to the fungicide component ranges from 35:31.25 to 8.75:31.25;
  when the fungicide is flutriafol, the weight ratio of the pyridine carboxylic acid herbicide component to the fungicide component ranges from 35:21.5 to 8.75:21.25;
  when the fungicide is kresoxim-methyl, the weight ratio of the pyridine carboxylic acid herbicide component to the fungicide component ranges from 35:25 to 8.75:25;
  when the fungicide is mancozeb, the weight ratio of the pyridine carboxylic acid herbicide component to the fungicide component ranges from 35:281.25 to 8.75:281.25;
  when the fungicide is metconazole, the weight ratio of the pyridine carboxylic acid herbicide component to the fungicide component ranges from 35:22.5 to 8.75:22.5;
  when the fungicide is metrafenone, the weight ratio of the pyridine carboxylic acid herbicide component to the fungicide component ranges from 17.5:37.5 to 8.75:37.5;
  when the fungicide is prochloraz, the weight ratio of the pyridine carboxylic acid herbicide component to the fungicide component ranges from 35:101.25 to 8.75:101.25;
  when the fungicide is propiconazole, the weight ratio of the pyridine carboxylic acid herbicide component to the fungicide component ranges from 35:31.25 to 8.75:31.25;
  when the fungicide is proquinazid, the weight ratio of the pyridine carboxylic acid herbicide component to the fungicide component ranges from 35:12.5 to 8.75:12.5;
  when the fungicide is prothioconazole, the weight ratio of the pyridine carboxylic acid herbicide component to the fungicide component ranges from 35:50 to 8.75:50;
  when the fungicide is pyraclostrobin, the weight ratio of the pyridine carboxylic acid herbicide component to the fungicide component ranges from 35:18.25 to 8.75:18.75;
  when the fungicide is quinoxyfen, the weight ratio of the pyridine carboxylic acid herbicide component to the fungicide component ranges from 35:37.5 to 8.75:37.5;
  when the fungicide is spiroxamine, the weight ratio of the pyridine carboxylic acid herbicide component to the fungicide component ranges from 35:180 to 8.75:180;
  when the fungicide is tebuconazole, the weight ratio of the pyridine carboxylic acid herbicide component to the fungicide component ranges from 35:31.25 to 35:250;
  when the fungicide is trifloxystrobin, the weight ratio of the pyridine carboxylic acid herbicide component to the fungicide component ranges from 35:62.5 to 8.75:62.5;
  when the fungicide is the picolinamide fungicide of formula (II), the weight ratio of the pyridine carboxylic acid herbicide component to the fungicide component ranges from 35:40.5 to 8.75:40.5;
  when the fungicide is fenpropidin, the weight ratio of the pyridine carboxylic acid herbicide component to the fungicide component is 17.5:562.5;

when the fungicide is iprodione, the weight ratio of the pyridine carboxylic acid herbicide component to the fungicide component is 17.5:750;

when the fungicide is picoxystrobin, the weight ratio of the pyridine carboxylic acid herbicide component to the fungicide component is 17.5:250;

when the fungicide is tetraconazole, the weight ratio of the pyridine carboxylic acid herbicide component to the fungicide component is 17.5:125; and when the fungicide is thiophanate-methyl, the weight ratio of the pyridine carboxylic acid herbicide component to the fungicide component is 17.5:750.

32. The method of claim 31, wherein the undesirable vegetation is controlled in cereals.

33. The method of claim 31, wherein the components of the synergistic herbicide/fungicide mixture are applied either separately or as part of a multipart herbicidal system.

34. The method of claim 31, wherein the synergistic herbicide/fungicide mixture is applied at an application rate of between about 10 grams per hectare (g/ha) and about 1235 g/ha based on the total amount of the pyridine carboxylic acid of formula (I) component and the fungicide component.

35. The method of claim 34, wherein the fungicide component is applied at an application rate of between about 60 g/ha and about 1200 g/ha and the pyridine carboxylic acid of formula (I) component is applied at an application rate of between about 1 g/ha and about 35 g/ha.

36. The method of claim 31, further comprising contacting the vegetation or the locus thereof with or applying to the soil or water an herbicide safener.

37. The method of claim 36, wherein a safener component is applied at an application rate of between about 0.05 g/ha and about 35 g/ha.

* * * * *